United States Patent [19]

Kershner et al.

[11] Patent Number: 4,897,481

[45] Date of Patent: Jan. 30, 1990

[54] PROCESS FOR THE MINIMIZATION OF RACEMIZATION IN THE PREPARATION OF OPTICALLY ACTIVE ((ARYLOXY)PHENOXY)PROPIONATE HERBICIDES

[75] Inventors: Larry D. Kershner; Jimmy J. Tai, both of Midland, Mich.

[73] Assignee: The Dow Chemical Company, Midland, Mich.

[21] Appl. No.: 200,400

[22] Filed: May 31, 1988

[51] Int. Cl.$^4$ .................. C07D 241/36; C07D 213/78; C07D 277/68; C07C 69/76

[52] U.S. Cl. ..................................... 544/354; 546/302; 548/170; 548/221; 558/414; 560/55; 560/60

[58] Field of Search .................. 546/302; 558/414; 544/354; 548/170, 221; 560/55, 60

[56] References Cited

U.S. PATENT DOCUMENTS

| | | | |
|---|---|---|---|
| 4,046,553 | 9/1977 | Takahashi et al. | 544/131 |
| 4,332,960 | 6/1982 | Trosken et al. | 560/62 |
| 4,332,961 | 6/1982 | Takahashi et al. | 560/62 |
| 4,477,276 | 10/1984 | Willms et al. | 71/94 |
| 4,523,017 | 6/1985 | Johnston et al. | 546/302 |
| 4,531,969 | 7/1985 | Nestler et al. | 71/108 |
| 4,550,192 | 10/1985 | Rogers et al. | 560/62 |
| 4,565,568 | 1/1986 | Johnston et al. | 71/94 |
| 4,600,432 | 7/1986 | Akahira et al. | 71/94 |
| 4,609,396 | 9/1986 | Fawzi | 71/92 |
| 4,629,493 | 12/1986 | Ura et al. | 544/131 |

FOREIGN PATENT DOCUMENTS

| | | | |
|---|---|---|---|
| 0001473 | 4/1979 | European Pat. Off. | 71/92 |
| 0003890 | 9/1979 | European Pat. Off. | 71/92 |

*Primary Examiner*—Mary C. Lee
*Assistant Examiner*—J. Richter
*Attorney, Agent, or Firm*—Craig E. Mixan; Ronald G. Brookens

[57] ABSTRACT

One of the routes to prepare optically active 2-(4-aryloxyphenoxy)propionic acid ester herbicide is to couple optically active 2-(4-hydrophenoxy)propionic acid esters with halogenated aromatic or heteroaromatic compounds. Conversion of the optically active 2-(4-hydroxyphenoxy)propionic acid ester into the acid salt prior to the coupling step effectively prevents the racemization that unexpectedly occurs otherwise.

4 Claims, No Drawings

PROCESS FOR THE MINIMIZATION OF RACEMIZATION IN THE PREPARATION OF OPTICALLY ACTIVE ((ARYLOXY)PHENOXY)PROPIONATE HERBICIDES

FIELD OF INVENTION

This invention relates to the preparation of optically active 2-(aryloxyphenoxy)propionic acids and derivatives thereof which are useful as herbicides. More specifically, this invention relates to an improved process which minimizes racemization during the preparation of these herbicides.

BACKGROUND OF THE INVENTION

The herbicidal activity of 2-(4-aryloxyphenoxy)propionic acids and derivatives thereof is well known in the art. Furthermore, optical isomers are often known to exhibit enhanced herbicidal activity over the corresponding racemates. For example, U.S. Pat. No. 4,531,969 discloses that the R-enantiomers of certain 2-(4-aryloxyphenoxy)propionic acids and certain derivatives thereof are distinguished by a considerably enhanced herbicidal action compared to the racemic modifications. Since reduced quantities of herbicide are required to achieve comparable levels of control, the application of mixtures enriched in the more efficacious R-enantiomer offers both economical and environmental advantages. Various methods for obtaining high concentrations of optical isomers are known. In addition to the resolution of a racemic mixture into its optically active components which, for example, depends on the conversion to diastereomers and subsequent physical separation, individual enantiomers can be obtained by direct synthesis employing an appropriate optically active starting material. For example, optically active alkyl 2-(4-aryloxyphenoxy)propionates are conveniently prepared by reaction of either an optically active alkyl 2-halopropionate or an optically active lactate ester of an alkyl or aryl sulfonate with a 4-aryloxyphenol as depicted in Equation 1 where the leaving group is a halogen or an alkyl or aryl sulfonate. The * represents an asymmetric carbon atom.

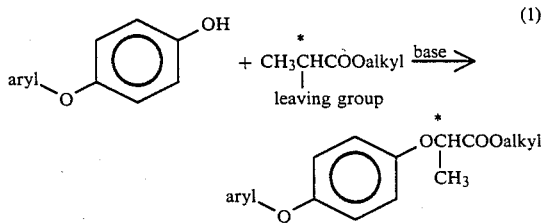

Theoretically, one can obtain essentially 100 percent of the desired enantiomer by this method. In practice, however, the optical purity of the final product is largely influenced by such factors as the optical purity of the starting material and the specific reaction conditions. Typically one obtains products containing a ratio of from 70 to 90 percent of the desired enantiomer and, correspondingly, from 10 to 30 percent of the other optical isomer. Such products are then said to possess an optical purity of 40 to 80 percent, i.e., from 40 to 80 percent of the mixture is the desired enantiomer and from 20 to 60 percent is a racemic mixture.

Partial racemization over the course of a reaction is somewhat typical of nucleophilic displacement reactions which involve the breaking and making of bonds at the asymmetric carbon atom of the starting material. Although such reactions mechanistically involve inversion of configuration, minor complications such as competing reactions can significantly adulterate the optical purity of the product.

An alternative approach for preparing optically active alkyl 2-(4-aryloxyphenoxy)propionates involves the reaction of an optically active alkyl 2-(4-hydroxyphenoxy)propionate with an aryl substrate having a leaving group activated with respect to aromatic nucleophilic substitution. This reaction is illustrated in Equation 2.

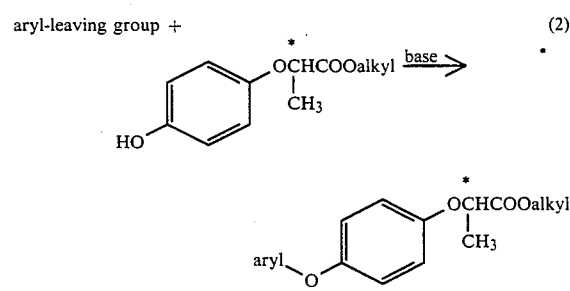

Since this reaction does not involve bond-breaking or bond-making with the asymmetric carbon atom of the optically active 2-(4-hydroxyphenoxy)propionate, very little if any racemization is expected, particularly in the presence of such relatively mild bases as the alkali metal carbonates which are typically used in such reactions. Unexpectedly, it has now been recognized that racemization during this reaction can be appreciable, especially for esters, i.e., when R is a lower alkyl group. The extent of racemization is dependent on the reaction conditions and on the type of aryl substrate employed.

Probably one of the most conventional ways to reduce the occurrence of racemization is to lower the reaction temperature. Such conventional practice, however, is not thoroughly effective and contributes to greatly extended reaction times. A more efficient and effective solution to this problem is desirable.

SUMMARY OF THE INVENTION

The present invention is directed to an improved process for minimizing the amount of racemization which occurs during in the preparation of herbicidal 2-(4-aryloxyphenoxy)propionic acid esters. More particularly, the present invention is directed to an improved process for reducing the amount of racemization in the preparation of an optically active 2-(4-aryloxyphenoxy)propionic acid ester of Formula (I)

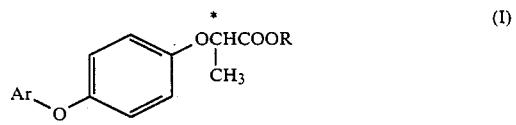

wherein
Ar represents an aryl group activated toward aromatic nucleophilic substitution reactions, and
R represents a straight-chained or branched alkyl group of from 1 to 8 carbon atoms inclusive or an alkoxyalkyl group of from 3 to 8 carbon atoms inclusive, which comprises contacting an alkali metal salt of optically active 2-(4-hydroxyphenoxy)propionic acid of Formula (II)

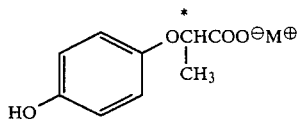
(II)

wherein
M⊕ represents Li⊕, Na⊕ or K⊕ with a halogenated aromatic compound of Formula (III)

Ar—X (III)

wherein
Ar is as previously defined and
X represents F, Cl, Br or I
in a polar aprotic organic solvent in the presence of at least one equivalent of an alkali metal carbonate; and subsequently esterifying the resulting 2-(4-aryloxyphenoxy)propionic acid alkali metal salt.

DETAILED DESCRIPTION OF THE INVENTION

One of the routes to prepare optically active 2-(4-aryloxyphenoxy)propionic acid ester herbicides is to couple optically active 2-(4-hydroxyphenoxy)propionic acid esters with halogenated aromatic or heteroaromatic compounds. Surprisingly, we have found that racemization occurs at this step. The extent of racemization depends on the reaction conditions and the kind of aromatic compound used. Typically, the slower the reaction under given conditions, the greater the extent of racemization. Thus, for example, the poorer the leaving group on the aryl halide, the slower the reaction and the greater the extent of racemization. The present invention converts the 2-(4-hydroxyphenoxy)propionic acid ester into an alkali metal salt of the 2-(4-hydroxyphenoxy)propionic acid prior to reacting with the halogenated aromatic compound. Conversion of the optically active (hydroxyphenoxy)propionate to the acid salt prior to the coupling step effectively prevents racemization.

Therefore, the present invention is directed to a process for reducing the amount of racemization during the preparation of an optically active 2-(4-aryl-oxyphenoxy)propionic acid ester of Formula (I)

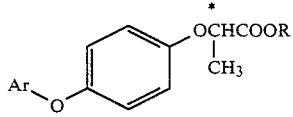
(I)

wherein
Ar represents an aryl group activated toward aromatic nucleophilic substitution reactions, and
R represents a straight-chained or branched alkyl group of from 1 to 8 carbon atoms inclusive or an alkoxyalkyl group of from 3 to 8 carbon atoms inclusive,
which comprises contacting an alkali metal salt of optically active 2-(4-hydroxyphenoxy)propionic acid of Formula (II)

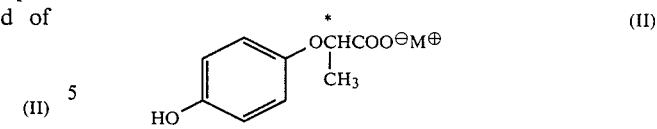
(II)

wherein
M⊕ represents Li⊕, Na⊕ or K⊕ with a halogenated aromatic compound of Formula (III)

wherein
Ar is as previously defined and
X represents F, Cl, Br or I
in a polar aprotic organic solvent in the presence of at least one equivalent of an alkali metal carbonate; and subsequently esterifying the resulting 2-(4-aryloxyphenoxy)propionic acid alkali metal salt.

As used herein, an aryl group activated toward aromatic nucleophilic substitution reactions refers to aromatic groups bearing electron withdrawing substituents or heteroaromatic groups, optionally bearing electron withdrawing substituents which readily react with oxygen nucleophiles.

The 2-(4-aryloxyphenoxy)propionic acid esters and the corresponding aryl halide starting materials to which the present method may be applied are disclosed, for example, in U.S. Pat. Nos. 4,046,553, 4,332,960, 4,332,961, 4,477,276, 4,523,017, 4,531,969, 4550,192, 4,565,568, 4,600,432, 4,609,396 and 4,629,493 and European Patent Application Publication Nos. 483, 1,473 and 3,890.

Particularly valuable examples of 2-(4-aryloxyphenoxy)propionic acid esters to which the present method may be applied are of Formula (IV)-(VII):

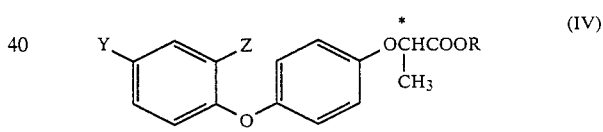
(IV)

wherein
Y is CF₃, CN or NO₂,
Z is H, F, Cl, Br or I, and
R is as previously defined;

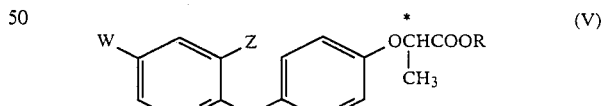
(V)

wherein
W is CF₃, F, Cl, Br or I and
Z and R are as previously defined;

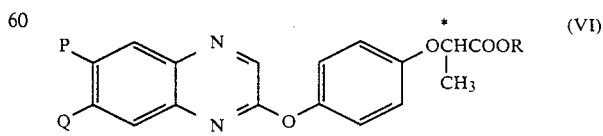
(VI)

wherein
P and Q are independently H, F, Cl, Br or I and
R is as previously defined; and

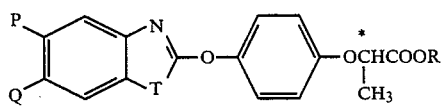

(VII)

wherein
T is O or S, and
P, Q and R are as previously defined.

For compounds of Formula (IV), Y is preferably $CF_3$ or CN and Z is preferably F or Cl.

For compounds of Formula (V), W is preferably $CF_3$, Cl, Br or I and Z is preferably H, F or Cl.

For compounds of Formula (VI), one of P or Q is preferably F or Cl.

For compounds of Formula (VII), one of P or Q is preferably F or Cl and T is preferably O.

By alkali metal is meant lithium, sodium and potassium. The preferred alkali metal carbonates and the corresponding alkali metal salts of 2-(4-hydroxyphenoxy)propionic acid are those of sodium and potassium.

By halogen is meant fluorine, chlorine, bromine and iodine. The preferred halogen leaving groups on the halogenated aromatic starting materials are fluorine and chlorine.

Polar aprotic organic solvents suitable for the present process include such functional groups as ketones, amides, sulfoxides, sulfones, nitriles, phosphoramides and the like. Specific examples of such polar aprotic organic solvents include but are not limited to acetone, methyl iso-butylketone (MIBK), dimethyl formamide (DMF), dimethyl acetamide (DMA), N-methyl pyrrolidone (NMP), dimethyl sulfoxide (DMSO), sulfolane, acetonitrile (ACN) and hexamethyl phosphoramide (HMPA). Preferred solvents are DMF, NMP, DMSO and ACN.

As used herein the term esterifying the resulting 2-(4-aryloxyphenoxy)propionic acid alkali metal salt means converting the alkali metal propionic acid into a straight-chained or branched alkyl ester of from 1 to 8 carbon atoms inclusive or into an alkoxyalkyl ester of from 3 to 8 carbon atoms inclusive by conventional esterification procedures. Typical esterification procedures are described, for example, in 'Advanced Organic Chemistry:Reactions, Mechanisms, and Structure' by Jerry March, 3rd Edition, John Wiley & Sons, New York, 1985, pp. 348-351, 353-354. Any conventional esterification procedure is contemplated provided racemization does not occur.

For example, the alkali metal salt of the propionic acid can be reacted directly with a primary or secondary alkyl bromide or iodide in a polar aprotic solvent to provide high yields of the carboxylic ester. This reaction is preferably carried out without isolation of the propionic acid salt.

Alternatively, the propionic acid salt can be neutralized to the carboxylic acid which, in turn, upon reaction with an appropriate alcohol, preferably in the presence of a dehydrating agent, produces the desired ester.

The alkali metal salt of 2-(4-hydroxyphenoxy)propionic acid can be prepared by neutralization with at least one equivalent of alkali metal carbonate either prior to or concomitant with admixture with the halogenated aromatic starting material. Alternatively, the alkali metal salt of 2-(4-hydroxyphenoxy)propionic acid can be prepared in advance by saponification of the corresponding ester.

The alkali metal salt of 2-(4-hydroxyphenoxy)propionic acid is contacted with about an equal molar amount of the aryl halide starting material in a polar aprotic solvent in the presence of at least an additional equivalent of alkali metal carbonate over and above the one equivalent that may have been used to neutralize the corresponding acid in situ. Therefore, at least 2 equivalents of carbonate are needed for each equivalent of the propionic acid when the propionic acid is neutralized in situ. Similarly, at least one equivalent of carbonate is needed if the alkali metal salt of 2-(4-hydroxyphenoxy)propionic acid has been pre-formed.

The reaction can generally be conducted from ambient temperature to about 120° C. Preferred temperatures range from about 50° C. to about 85° C.

The reaction can be conducted at subatmospheric or superatmospheric pressures, but atmospheric pressure is satisfactory and preferred.

The resulting 2-(4-aryloxyphenoxy)propionic acid salt can be directly esterified by treatment with an appropriate alkyl bromide or iodide or dimethyl sulfate can be neutralized to the acid, which, upon isolation, can be esterified by conventional techniques.

The following examples further illustrate the present invention and are not to be construed as a limitation thereon.

EXAMPLE 1

Preparation of R-Methyl 2-(4-(2'-fluoro-4'-cyanophenoxy)phenoxy)propionate

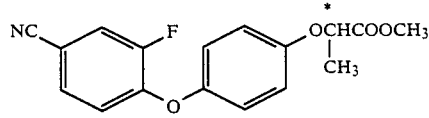

The R-enantiomer of 2-(4-hydroxyphenoxy)propionic acid [9.2 grams (g); R/S =97/3] and 3,4-difluorobenzonitrile [6.9 g] was dissolved in 50 milliliters (mL) of DMSO. Potassium carbonate [16.0 g] was added and the reaction mixture was heated to 85° C. and kept at that temperature for 2 hours (h). After cooling to room temperature, the solids were removed by filtration and 100 mL of water was added to dilute the solution. The pH of the aqueous solution was adjusted to less than 1.0 with concentrated HCl and the product was isolated from the acidic aqueous mixture by extraction with toluene. Evaporation of the solvent provided 14.1 g of product.

The R-2-(4-(2'-fluoro-4'-cyanophenoxy)phenoxy)propionic acid is converted to the methyl ester by treatment at reflux with a large excess of methanol in the presence of a catalytic amount of Dowex MSC-1 H+ ion exchange resin and enough 2,2-dimethoxypropane to remove the by-product water. After less than 1 percent free acid remains the mixture is cooled and the resin catalyst is removed by filtration. Evaporation of the volatile components of the filtrate leaves the desired methyl ester. Methyl ester prepared in this manner has an enantiomeric ratio (R/S) of 97/3.

EXAMPLE 2

Preparation of R-Methyl 2-(4-(2'-fluoro-4'-cyanophenoxy)phenoxy)propionate

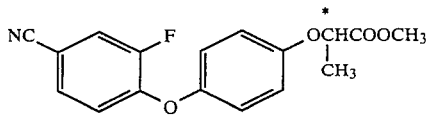

To a mixture of 34 g of potassium carbonate in 70 mL of DMSO ws added 13.0 g of R-2-(4-hydroxyphenoxy)-propionic acid [R/S =99.5/0.5] and 10 g of 3,4-difluorobenzonitrile. The mixture was heated to 95° C. and kept at that temperature for 6 h. The solids were removed by filtration, and the filtrate was cooled to ambient temperature and treated with 14.8 g of methyl iodide. After 2 h at ambient temperature, water was added to the solution.

The resulting aqueous mixture was extracted twice with perchloroethylene. The organic extract was washed with water and the solvent was evaporated to give 20.5 g of the desired methyl ester having an R/S enantiomer ratio of 99.5/0.5 as determined by high pressure liquid chromatography (HPLC) using a chiral column packing.

EXAMPLE 3

Preparation of R-Methyl 2-(4-((3-chloro-5-trifluoromethyl-2-pyridinyl)oxy)-phenoxy)propionate

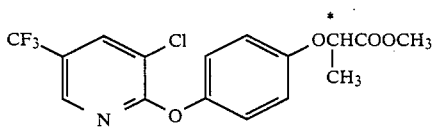

To a mixture of 257 g of potassium carbonate in 500 mL of DMSO was added 130 g of R-2-(4-hydroxyphenoxy)propionic acid [R/S =99.5/0.5] and 154.3 g of 2,3-dichloro-5-trifluoromethylpyridine. The mixture was heated to 95° C. and kept at that temperature for 6 h. The solids were removed by filtration, and the filtrate was cooled to ambient temperature and treated with 148 g of methyl iodide. After 2 h at ambient temperature, water was added to the solution. The resulting aqueous mixture was extracted twice with perchloroethylene. The organic extract was washed with water and the solvent was evaporated to give 235 g of the desired methyl ester having an R/S ratio of 99.4/0.6.

Various modifications may be made in the present invention without departing from the scope thereof and it is understood that we limit ourselves only as defined in the appended claims.

What is claimed is:

1. A process for reducing the amount of racemization in the preparation of an optically active 3-(4-aryloxyphenoxy)propionic acid ester of formula (I)

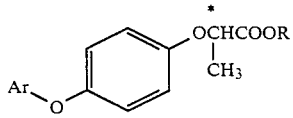 (I)

wherein

Ar represents an aryl group activated toward aromatic nucleophilic substitution reactions, and R represents a straight-chained or branched alkyl group of from 1 to 8 carbon atoms inclusive or an alkoxyalkyl group having a total of from 3 to 8 carbon atoms inclusive, which comprises contacting an alkali metal salt of optically active 2-(4-hydroxyphenoxy)propionic acid of formula (II)

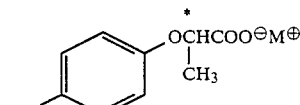 (II)

wherein $M^{\oplus}$ represents $Li^{\oplus}$, $Na^{\oplus}$ or $K^{\oplus}$ with a halogenated aromatic compound of formula (III)

Ar—X (III)

wherein

Ar is as previously defined and

X represents F, Cl, Br or I in a polar aprotic organic solvent in the presence of at least one equivalent of an alkali metal carbonate; and subsequently esterifying the resulting 2-(4-aryloxyphenoxy)propionic acid alkali metal salt.

2. The process of claim 1 in which the aryl group, Ar, is selected from the group represented by the formulae (IV)–(VII):

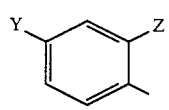 (IV)

wherein

Y represents $CF_3$ or CN, or $NO_2$, and

Z represents H, F, Cl, Br or I;

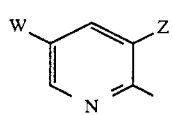 (V)

wherein

W is $CF_3$, F, Cl, Br or I and

Z is previously defined;

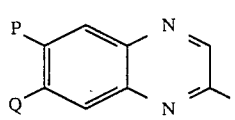 (VI)

wherein

P and Q are independently H, F, Cl, Br or I; and

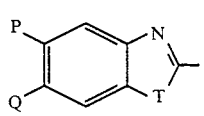 (VII)

wherein

T represents O or S, and

P and Q are as previously defined.
3. The process of claim 2 in which Ar represents
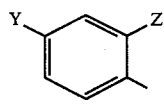 (IV)
wherein
Y represents $CF_3$ or CN, and
Z represents F or Cl.
4. The process of claim 2 in which Ar represents
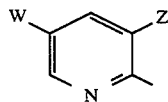 (V)
wherein
W represents $CF_3$, Cl, Br or I, and
Z represents H, F or Cl.
* * * * *